(12) United States Patent
Narai et al.

(10) Patent No.: US 7,207,223 B2
(45) Date of Patent: Apr. 24, 2007

(54) TOROIDAL-TYPE CONTINUOUSLY VARIABLE TRANSMISSION COMPONENT AND METHOD FOR EVALUATING THE SAME

(75) Inventors: Hiroshi Narai, Kanagawa (JP); Kikuaki Kamamura, Nara (JP)

(73) Assignee: NSK Ltd., Tokyo (JP)

( * ) Notice: Subject to any disclaimer, the term of this patent is extended or adjusted under 35 U.S.C. 154(b) by 283 days.

(21) Appl. No.: 10/803,920

(22) Filed: Mar. 19, 2004

(65) Prior Publication Data

US 2004/0176210 A1 Sep. 9, 2004

Related U.S. Application Data

(62) Division of application No. 09/617,310, filed on Jul. 14, 2000, now abandoned.

(30) Foreign Application Priority Data

Jul. 14, 1999 (JP) .............................. P. 11-200409

(51) Int. Cl.
*G01N 29/07* (2006.01)
(52) U.S. Cl. .......................................... 73/593; 73/602
(58) Field of Classification Search .................. 73/593, 73/622, 602
See application file for complete search history.

(56) References Cited

U.S. PATENT DOCUMENTS 5,056,368 A * 10/1991 Kawasaki et al. ............. 73/642
5,147,140 A    9/1992 Murakami et al.
5,228,004 A *  7/1993 Kawasaki ..................... 367/13
5,298,323 A    3/1994 Narai et al.
5,855,531 A    1/1999 Mitamura et al.
6,065,343 A *  5/2000 Kiuchi et al. .................. 73/622
6,113,514 A    9/2000 Okubo et al.
6,165,100 A * 12/2000 Mitamura et al. ............. 476/72
6,276,210 B2   8/2001 Kiuchi et al.
6,318,178 B1 * 11/2001 Kato et al. ..................... 73/602
6,439,054 B1 *  8/2002 Gore et al. ..................... 73/620
6,443,870 B1 *  9/2002 Yoshikawa et al. ............ 476/40
7,017,414 B2 *  3/2006 Falsetti et al. ................. 73/600
2001/0001172 A1* 5/2001 Kiuchi et al. .................. 73/593

FOREIGN PATENT DOCUMENTS

JP           6-287710 A       10/1994
JP          11-190408 A        7/1999
JP          11337530 A   *   12/1999

* cited by examiner

*Primary Examiner*—Hezron Williams
*Assistant Examiner*—Rose M. Miller
(74) *Attorney, Agent, or Firm*—Sughrue Mion, PLLC (57) ABSTRACT

A toroidal-type continuously variable transmission component, such as an input disk, an output disk, an inner ring of a power roller bearing, and an outer ring of the power roller bearing, which is functioned as a rolling member, has a layer a depth of which is 0.5 mm or less from the surface thereof. The layer does not include a non-metallic inclusion having a maximum diameter of up to 0.1 mm in the area thereof having a depth of 0.5 mm or less from the surface thereof.

8 Claims, 10 Drawing Sheets

DETECTING DIRECTION
DETECT
TP1
30

FIG.8

ULTRASONIC DETECTION RESULT NEAR SURFACE PERPENDICULAR DETECT (WATER DISTANCE 20mm)

DETECTING DIRECTION
DETECT
TP2
40

FIG.12

ULTRASONIC DETECTION RESULT NEAR SURFACE PARALLEL DETECT (WATER DISTANCE 20mm)

TP3
50
(FORM HOLES OF
φ0.5mm AT DEPTHS
3,5,7 AND 9mm)

FIG.15

ULTRASONIC DETECTION RESULT WITHIN BEARING
INNER DETECT OF φ0.5mm (WATER DISTANCE 15mm)

TOROIDAL-TYPE CONTINUOUSLY VARIABLE TRANSMISSION COMPONENT AND METHOD FOR EVALUATING THE SAME

This is a divisional of application Ser. No. 09/617,310 filed Jul. 14, 2000 now abandoned; the disclosure of which is incorporated herein by reference.

BACKGROUND OF THE INVENTION

The present invention relates to a highly reliable continuously variable transmission (CVT) component, such as a disk and a power roller bearing for use in a toroidal-type continuously variable transmission (CVT), and a method for evaluating the same.

Since CVT disk and power roller are used under the high load and high surface pressure environment and are ranked as important safety parts, in order to prevent them against breakage and exfoliation in a short time of use, as the material of the CVT disk and power roller, there is used high-purity steel for a rolling bearing. In such high-purity steel, in order to extend the life of the rolling bearing as well as to enhance the reliability of the rolling bearing, the particle diameter distribution of oxide-system inclusions (the number and size of the inclusions) in a give area (or volume) to be sampled must be limited; and, therefore, for such limitation, there are proposed a large number of inclusion detect methods, for example, in Japanese Patent Unexamined Publication No. Hei. 3-56640, Japanese Patent Unexamined Publication No. Hei. 7-109541, Japanese Patent Unexamined Publication No. Hei.5-117804, and Japanese Patent Unexamined Publication No. Hei. 6-192790.

Conventionally, as an ultrasonic defect detect method for detecting the internal defects of a bearing ring, there is known a vertical defect detect method in which, in a process for manufacturing steel material for a bearing ring, ultrasonic waves are transmitted through the steel material after rolled from the outer peripheral surface thereof to the interior portion thereof under water or on a table to thereby detect the defects of the bearing ring (Special Steel, Vol. 46, No. 6, Page 31 published by Special Steel Club (Corporation)

By the way, although the high-purity steel for a rolling bearing is manufactured in a highly controlled line in order to remove non-metallic inclusions which give rise to the defects of the high-purity steel, actually, it is impossible to remove all of such defects. And, even in the high-purity steel, once in a great while, there can suddenly occur a defect and it is impossible to prevent such sudden occurrence of the defect completely. Especially, a large-size inclusion is fundamentally not allowed to exist in the vicinity of the surface of the high-purity steel because it gives rise to the bending fatigue rupture of the high-purity steel in a CVT disk. For this reason, it is necessary to check all of the CVT disks and power rollers for the defects thereof.

However, it is a main object of the above-mentioned conventional defect detect method to detect internal defects present in blow holes formed in the interior portion of the steel material or in the unrolled portion of the steel material left in the rolling process thereof, not to detect defects in the vicinity of the surface of the steel material, especially, large-size inclusions of the order of several hundred μm. This is partly because the surface of the steel material is rough just as it is rolled and thus, just below the surface of the steel material, an insensitive zone is large for the ultrasonic defect detect method, and also partly because the steel material includes bent and distorted portions and thus it is difficult to keep constant the distance between the steel material and a detect probe, especially, it is impossible to detect a micro-defect in the vicinity of the surface of the steel material. Also, in case where the interior portion of steel material having a large diameter of more than 100 mm is checked for the defect thereof, detecting frequencies must be lowered so as to prevent the sensitivity from lowering due to the attenuation of ultrasonic waves, so that nothing but the large-size defect having a size of several mm or so can be detected.

On the other hand, the main object of an ultrasonic defect detect method for a rolling body is to detect a surface flaw and a defect in the upper-most or extreme surface portion of the steel material with high efficiency. For example, using ultrasonic waves having high frequencies such as 50–150 MHz, a microscopic non-metallic inclusion having a size of up to 0.01 mm (10 μm) can be detected.

SUMMARY OF THE INVENTION

The present invention aims at eliminating the drawbacks found in the conventional defect detect methods. Accordingly, it is an object of the invention to provide an extended-life, highly reliable CVT component which is hard to produce exfoliation in the slide surface thereof. Also, it is another object of the invention to provide a method for evaluation of the highly reliable CVT component which can detect a non-metallic inclusion existing in the area of the CVT component, which is situated just below the surface of the CVT component, with high accuracy.

In attaining the above objects, according to one aspect of the invention, there is provided a highly reliable CVT component comprising a rolling member formed of steel for use in a toroidal-type continuously variable transmission, wherein the rolling member does not contain a non-metallic inclusion having a maximum diameter of 0.1 mm or more in the area thereof of 0.5 mm or less from the surface thereof.

In the above-mentioned toroidal-type continuously variable transmission component, it is preferable that the maximum diameter of non-metallic inclusion disposed within the layer is less than 0.1 mm.

The above object can also be achieved by a toroidal-type continuously variable transmission component, according to the present invention, comprising:

a rolling member made of steel and having a layer formed at 0.4 mm or less from the surface thereof, wherein the layer does not contain non-metallic inclusion having the maximum diameter of 0.115 mm or more.

In the above-mentioned toroidal-type continuously variable transmission component, it is preferable that the maximum diameter of non-metallic inclusion disposed within the layer is less than 0.115 mm.

Also, according to another aspect of the invention, there is provided a method for evaluating a highly reliable CVT component, in which the highly reliable CVT component comprising a rolling member formed of steel for use in a toroidal-type continuously variable transmission and an ultrasonic defect detect probe are disposed within an ultrasonic wave transmissive medium, an ultrasonic wave is radiated through the ultrasonic wave transmissive medium to the rolling member from the ultrasonic defect detect probe, and a defect existing in the surface and interior portion of the rolling member is detected and evaluated in accordance with an ultrasonic echo reflected by the rolling member, characterized in that an ultrasonic wave having a frequency in the range of 5 MHz–30 MHz is radiated onto the rolling member according to at least one of an oblique defect detect method and a vertical defect detect method, a non-metallic inclusion existing in the area of 0.5 mm or less from the surface of the rolling member is detected in accordance with the wave form of an ultrasonic echo reflected by the rolling member, and, when the thus detected non-metallic inclusion has a maximum diameter of 0.1 mm or more, the rolling member is disqualified.

Figure 5:
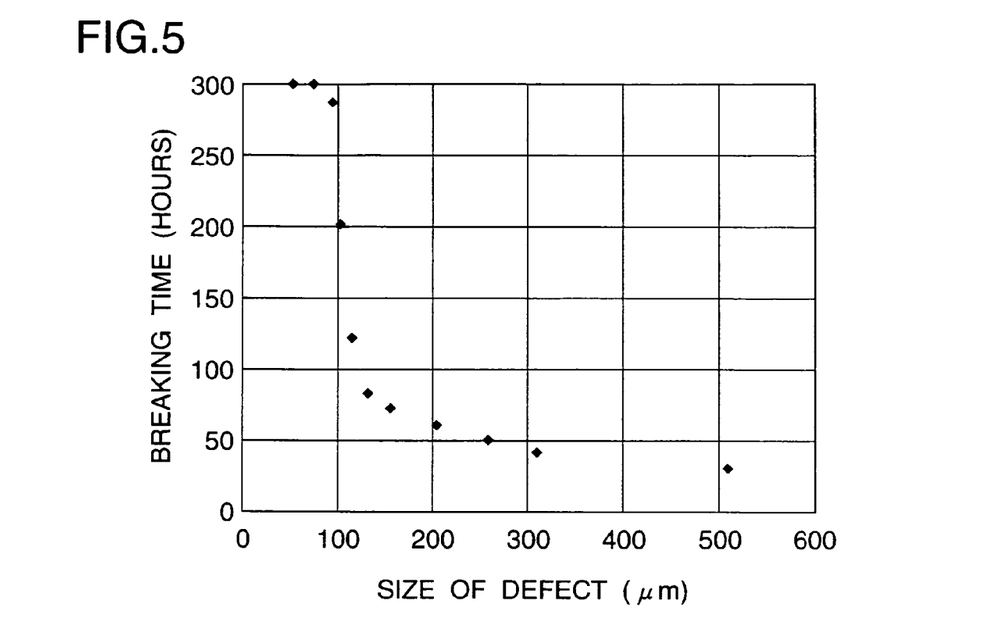
FIG. 5 is a characteristic view of the results of an evaluation test.
Figure 6:
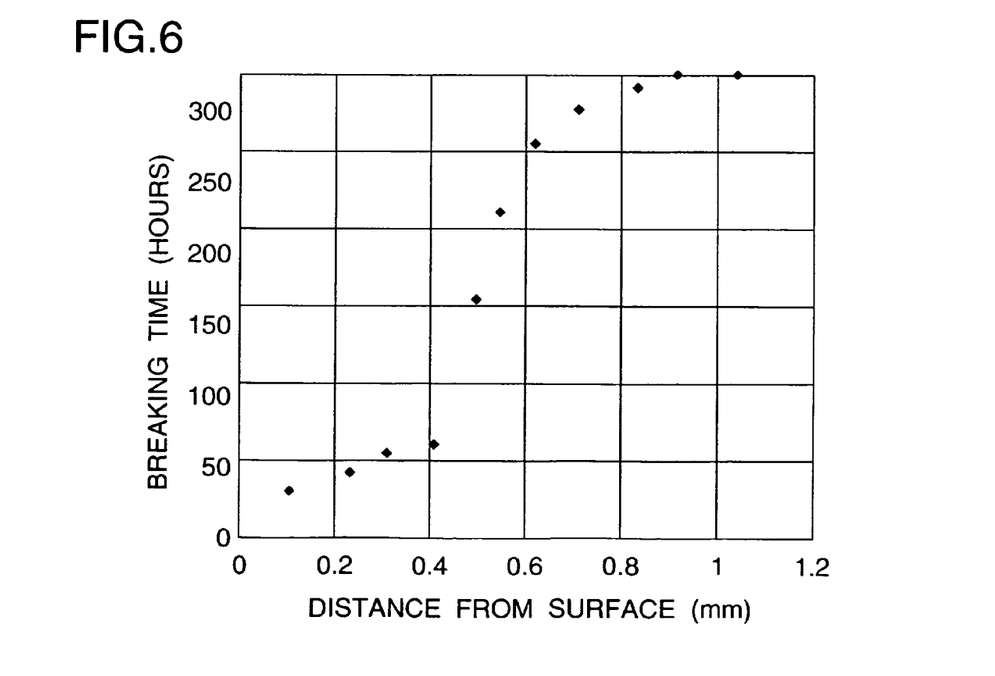
FIG. 6 is a characteristic view of the results of another evaluation test.

The present inventors et al. have made every efforts to study a method for detecting a non-metallic inclusion existing just below the slide surface of a CVT component (such as CVT disk and power roller) with high accuracy and have found that, in the area of 0.5 mm or less from the slide surface of the CVT component, even in case where the non-metallic inclusion is a macro inclusion of the order of 100 μm, it can give rise to bending fatigue rupture in the CVT component such as the CVT disk and power roller. That is, when the relations between the sizes of the defects and the breaking lives of the CVT disks obtained from our observation on the broken surfaces of the CVT disks are arranged, there are obtained such results as shown in FIG. 5; and, when the relations between the positions of the defects measured from the surfaces of the CVT disks and the breaking lives of the CVT disks are arranged, there are obtained such results as shown in FIG. 6. As can be seen clearly from FIG. 5, it has been found that, in case where the size of a defect (non-metallic inclusion) existing at a position of 0.5 mm from the surface of the CVT disk is more than 100 μm, the breaking life of the CVT disk is lowered sharply and heavily. Also, as can be seen clearly from FIG. 6, it has been found that, in case where the position of a defect (non-metallic inclusion) having a maximum diameter of 100 μm or less is larger than the range of 0.4–0.5 mm from the surface of the CVT disk, the breaking life of the CVT disk is enhanced sharply and heavily. From these discoveries, it has been confirmed that, in the case of a CVT component in which any defect having a size of 100 μm or more does not exist in the area of 0.4–0.5 mm from the surface thereof, the breaking life of the CVT component is extended.

On the other hand, the present inventors et al. have also made every effort to improve the ultrasonic defect detect method as a method for evaluating the CVT disk and power roller bearing. As a result, the inventors et al. have found that, even in the case of a frequency of the order of 10 MHz, by using an ultrasonic wave (surface wave) which is transmitted through the surface neighboring area of the CVT disk or power roller bearing, even a large size inclusion having a size of 100 μm or less which exceeds the conventional theoretical detect limit (½wave length) can be detected, provided that it exists in the surface wave reaching depth of 0.5 mm or less from the surface of the CVT disk or power roller bearing. That is, although the ultrasonic defect detect technique is widely used as a guarantee technique for the interior defects of iron and steel material, the frequency thereof is 5 MHz or less; as a defect detect method, the ultrasonic defect detect method includes an oblique defect detect method and a vertical defect detect method; and, the defect size to be detected is a base damage of 1 mm or more. Further, in case where the surface-just-below area (extreme surface) of the CVT disk or power roller bearing can be influenced by the surface roughness of the steel material of the CVT disk or power roller bearing to thereby provide an unsensitive area, which leads to the greatly lowered defect detect accuracy.

Further, there has been made an attempt to enhance the detect accuracy using a vertical defect detect method using a further higher frequency (CAMP-ISIJ Vol. 12 (1999)-437). However, in this case, not only the neighboring portion of the extreme surface provides an unsensitive area but also the attenuation of the ultrasonic wave is heavy, which makes it impossible to detect a defect in the deep portion of the CVT disk or power roller bearing.

The present inventors et al., in order to solve the above drawbacks found in the conventional ultrasonic defect detect methods, combined the oblique defect detect method with the vertical defect detect method using frequencies in the range of 5 MHz–30 MHz to thereby complete a highly reliable CVT component evaluation method capable of detecting defects over the whole section of the CVT component, such as the CVT disk or power roller bearing. After then, the present inventors et al. further improved this evaluation method to thereby find that, in the surface neighboring area of 0.5 mm or less from the surface of the CVT component, an inclusion having a size of 100 μm or less can be detected with no use of an ultrasonic wave having a high frequency of more than 30 MHz (U.S. Pat. No. 6,065,343). By the way, in case where the frequency of the ultrasonic wave goes below 5 MHz, it is very difficult to detect a small defect and, therefore, the lower limit value of the frequency is set at 5 MHz.

On the other hand, in case where the frequency of the ultrasonic wave exceeds 30 MHz, the ultrasonic wave attenuates greatly to thereby make it difficult to detect defects over the whole section of the CVT component and, for this reason, the upper limit value of the frequency is set at 30 MHz.

TABLE 1

| Defect No. | Size of Defects | Position of Defects |
|---|---|---|
| 1 | 50 μm | 0.1 mm |
| 2 | 100 μm | 0.6 mm |
| 3 | 80 μm | 0.2 mm |
| 4 | 150 μm | 0.4 mm |

By the way, in Table 1, there are shown the sizes and positions of the defects (non-metallic inclusions) that have been detected from the CVT disk according to the oblique surface wave method using a defect detect frequency of 10 MHz. Here, the sizes and positions of the defects were specified by grinding the defect detected portions.

Now, the subject matter of the present invention is to apply the characteristics of the oblique surface wave method to the problem relating to the bending fatigue breakage or rupture that is peculiar to the above-mentioned CVT disk. According to the invention, no existence of a large size inclusion having a size of 100 μm or more in the surface neighboring area of the CVT disk can be guaranteed at a relatively low cost by a non-rupture inspection method.

DETAILED DESCRIPTION OF THE PREFERRED EMBODIMENTS

Now, description will be given below of the preferred embodiments of a highly reliable CVT component and a method for evaluation of the highly reliable CVT component according to the invention with reference to the accompanying drawings.

Figure 1:
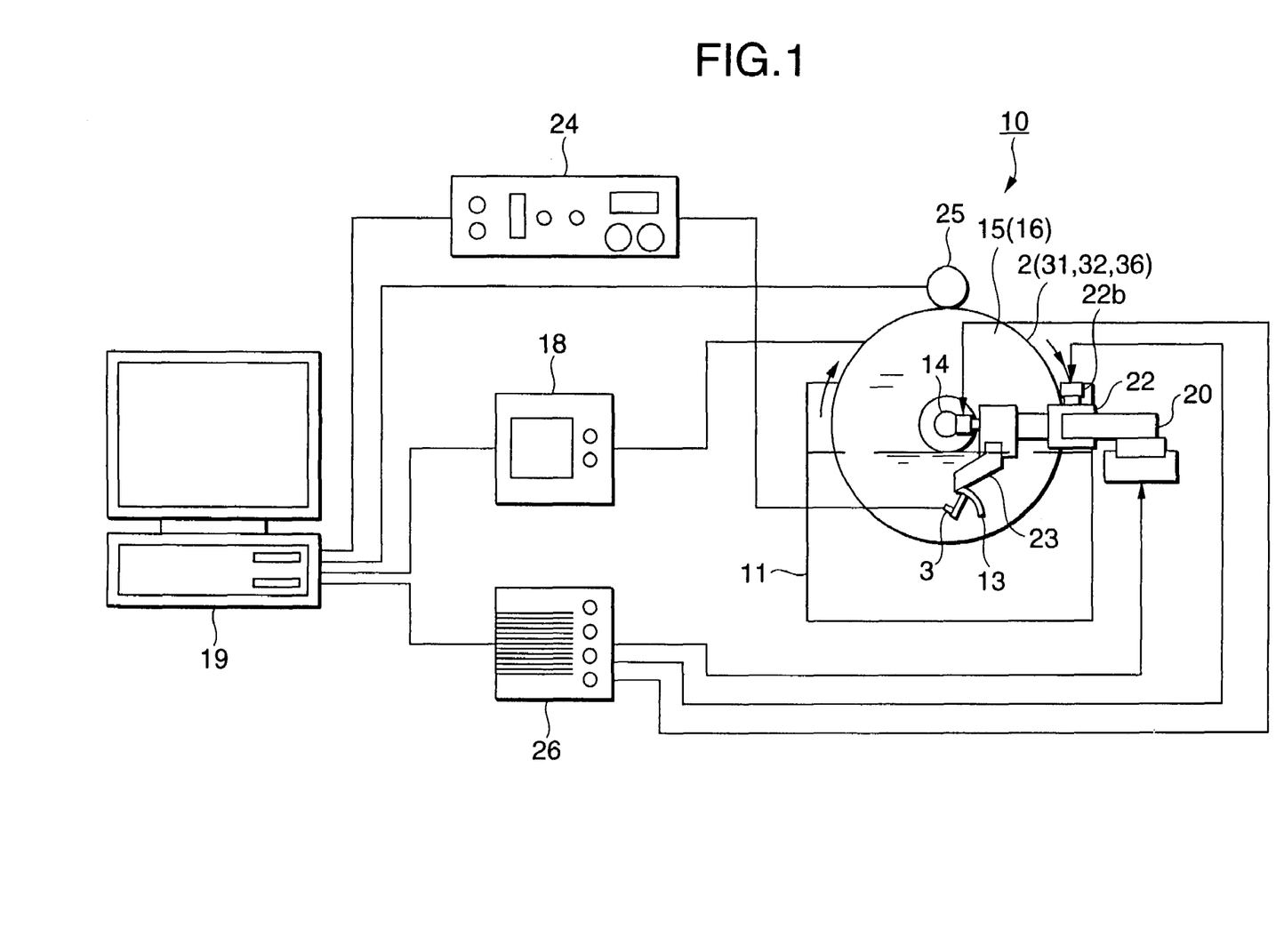
FIG. 1 is a structure block diagram of the outline of an evaluation test apparatus.

FIG. 1 is a schematic view of an ultrasonic defect detect apparatus. In FIG. 1, reference character 11 designates a water tank in which water serving as an ultrasonic wave transmission medium is stored. Within the water tank 11, there are disposed a CVT power disk (or a CVT power roller bearing) serving as a sample 2 and an ultrasonic probe 3 in such a manner that they are respectively immersed in the water.

The ultrasonic probe 3 includes a reflecting plate 13 formed in a parabola shape and also uses a focus type of probe which has strong directivity and is hard to be influenced by the curvature of the power disk 2. The power disk 2 is disposed on a turn table 15 (16) with the surface thereof facing the probe 3. The power disk 2 is coaxial with the rotary shaft of the turn table 15 (16), while the power disk 2 and turn table 15 (16) can be driven or rotated in synchronism with each other by a servo motor 14. By the way, reference character 18 designates a control amplifier which is used to drive the servo motor 14.

Figure 2:
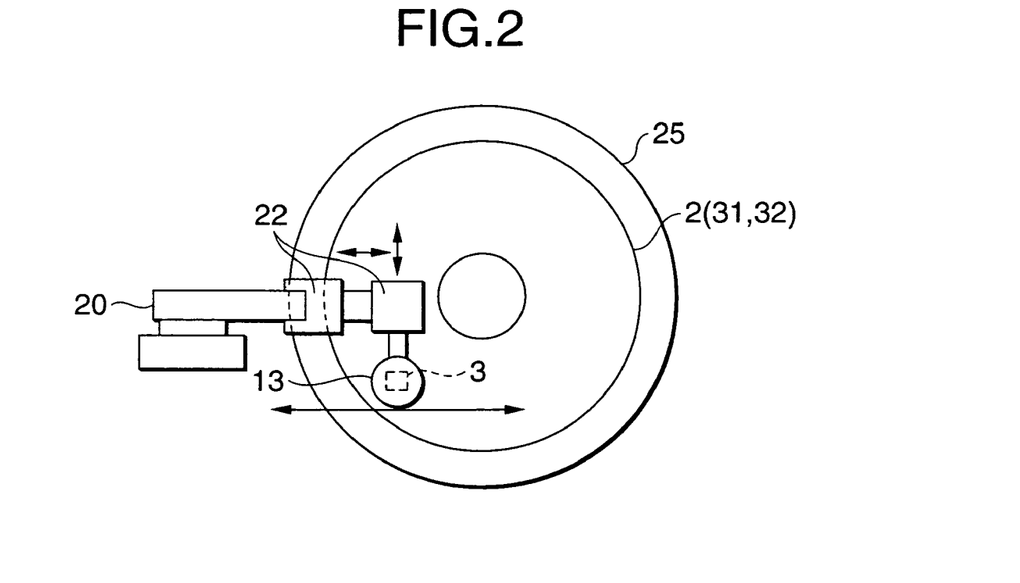
FIG. 2 is a section view of an inner race and an outer race respectively forming a bearing.
Figure 3:
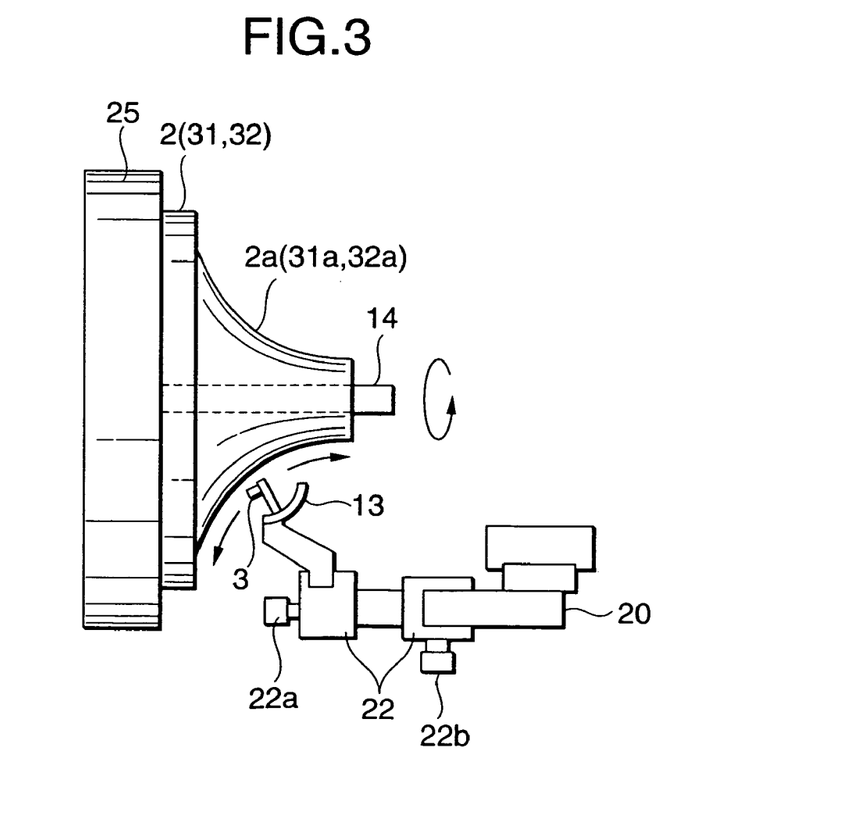
FIG. 3 is a partially enlarged section view of the above inner and outer races of the bearing.

As shown in FIGS. 2 and 3, the probe 3 is supported by a two-axis control type of XY table 22 which can be moved in both of the radial direction and axial direction of the power disk 2. The XY table 22 includes two drivers 22a, 22b which can be respectively controlled by a controller 26. These two drivers 22a, 22b are capable of moving the probe 3 together with the XY table 22 along the slide surface 2a of the power disk 2.

Further, the XY table 22 is movably supported by a linear guide device 20. The linear guide device 20 is capable of moving the ultrasonic defect detect probe 3 in the axial direction of the sample 2 through a servo motor (not shown) which can be controlled by a controller 26 for linear guide. In operation, in case where a rotary encoder 25 disposed on the outer peripheral surface of the sample 2 detects that the sample 2 has rotated once (360° C.), the linear guide controller 26 controls the servo motor in accordance with an instruction from a control unit 19 to thereby move the probe 3 only by a given distance in the axial direction of the sample 2. This makes it possible to detect defects over the whole cross section of the sample 2.

The probe 3 is connected to both of the input and output portions of an ultrasonic defect detect device 24. The probe 3 not only transmits an ultrasonic pulse corresponding to a voltage signal from the ultrasonic defect detect device 24 to the outer peripheral surface 2a of the disk 2, but also receives the reflected echo of the ultrasonic pulse, converts it into a voltage signal, and sends the voltage signal back to the ultrasonic defect detect device 24.

The ultrasonic defect detect device 24 not only transmits an instruction signal comprising a voltage signal to the ultrasonic defect detect probe 3 in accordance with an instruction from the control unit 19 (which comprises of a personal computer), but also sends back defect detect information, which is obtained in accordance with the transmitted and received signals, to the control unit 19. In response to this, the control unit 19 displays the wave form of an ultrasonic echo on a CRT screen.

The probe 3 is structured such that it can move by a given distance on a curved line previously determined according to the size of the disk 2 and thus can carry out a scan along the slide surface 2a of the disk 2. This makes it possible to detect the defects over the whole surface of the disk 2.

The defect detection was carried out according to a water immersion method using the following conditions.

That is:

Probe: Focus-type probe

Frequency: 10 MHz

And, the defect detection was performed in such a manner that the angle of refraction of an ultrasonic wave incident on the power disk surface 2a was set at an angle of 30° and the angle of refraction of the thus incident ultrasonic wave was set at an angle of 5°.

Figure 4:
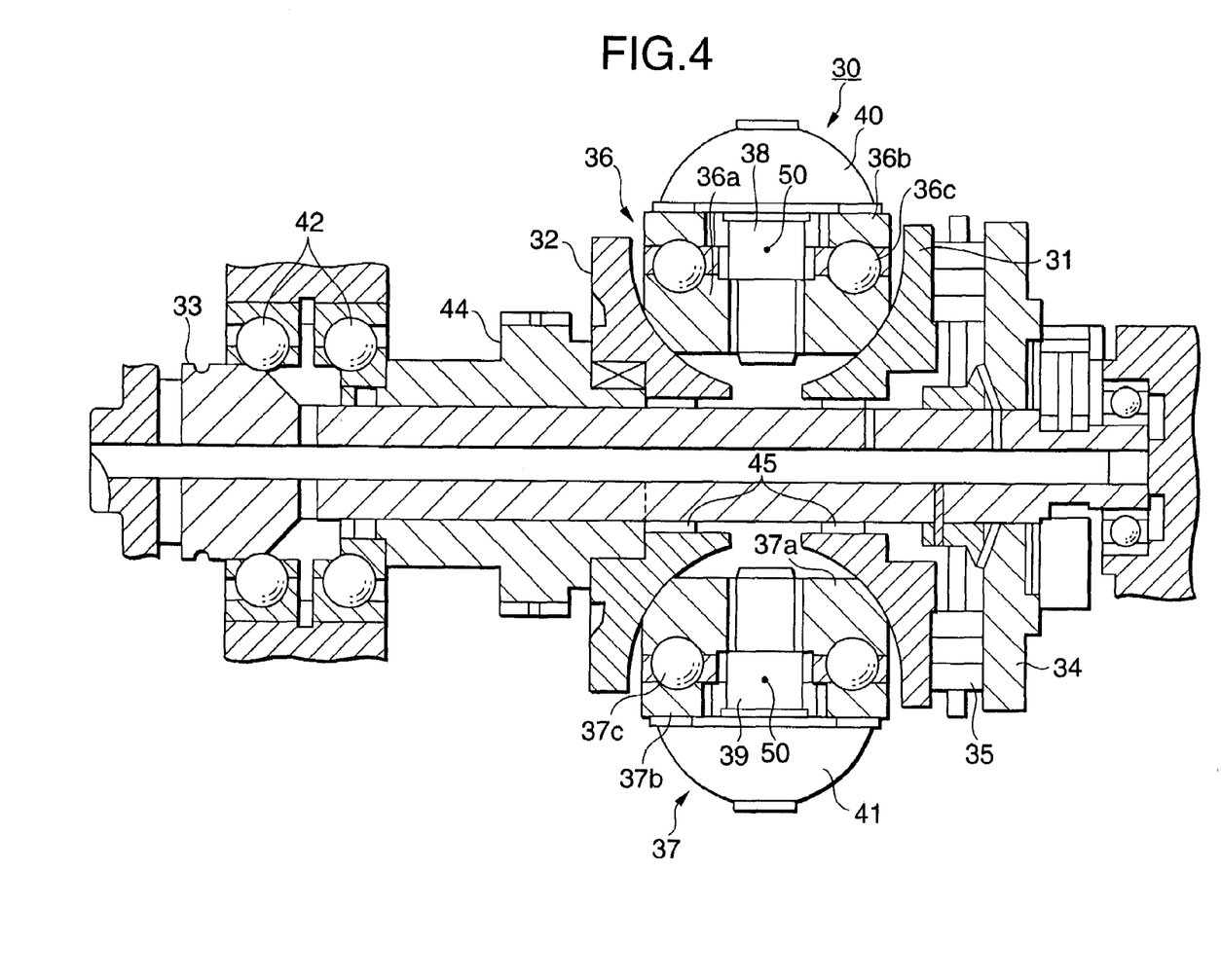
FIG. 4 is a schematic view of the structure of the evaluation test apparatus.

Next, using a disk which was confirmed by the above defect detection that a defect having a size of 100 μm or more was not present at all and a disk confirmed that a defect having a size of 100 μm or more was present, the evaluation of the durability of these two kinds of disks was made under the following conditions by a toroidal-type CVT apparatus 30 shown in FIG. 4.

(Evaluation Conditions)

Number of rotations of input shaft: 4000 rpm

Input torque: 350 N m

Oil used: Synthetic lubricant

Oil temperature: 100° C.

Now, description will be given below of the toroidal-type CVT 30 with reference to FIG. 4.

The toroidal-type CVT 30 has a structure that, within a housing (not shown), an input disk 31 and an output disk 32 are disposed on the same shaft but opposed to each other. An input shaft 33 is penetrated through the axial core portion of the toroidal transmission portion of the toroidal-type CVT apparatus 30 including the input disk 31 and output disk 32. On one end of the input shaft 33, there is disposed a loading cam 35. And, the loading cam 34 transmits the power (rotational force) of the input shaft 33 to the input disk 31 through a cam roller 35.

The input disk 31 and output disk 32 have substantially the same shape and are disposed symmetric. And, their mutually opposed surfaces are respectively formed as toroidal-shaped surfaces; that is, they cooperate together in such a manner that the axial section thereof has a substantially semicircular shape. Also, within a toroidal cavity which is defined by the toroidal-shaped surfaces of the input disk 31 and output disk 32, there are disposed a pair of power roller bearings 36 and 37 for operation transmission in such a manner that they are in contact with the input disk 31 and output disk 32.

By the way, the power roller bearing 36 is constituted by a power roller 36a (which corresponds to an inner race forming the power roller bearing 36) capable of rolling on the toroidal-shaped surfaces of the input disk 31 and output disk 32, an outer race 36b, and a plurality of rolling bodies (steel balls) 36c. On the other hand, the power roller bearing 37 is constituted by a power roller 37a (which corresponds to an inner race forming the power roller bearing 37) capable of rolling on the toroidal-shaped surfaces of the input disk 31 and output disk 32, an outer race 37b, and a plurality of rolling bodies (steel balls) 37c.

That is, the power roller 36a serves also as an inner race which is a component element of the power roller bearing 36, while the power roller 37a serves also as an inner race which is a component element of the power roller bearing 37. In this structure, the power roller 36a is pivotally and rotatably mounted on a trunnion 40 through a pivot shaft 38, the outer race 36b, and the plurality of rolling bodies 36c and, at the same time, the power roller 36a is supported in such a manner that it can be inclined about a pivot shaft 50 which serves as the center of the toroidal-shaped surfaces of the input and output disks 31 and 32.

On the other hand, the power roller 37a is pivotally and rotatably mounted on a trunnion 41 through a pivot shaft 39, the outer race 37b, and the plurality of rolling bodies 37c and, at the same time, the power roller 37a is supported in such a manner that it can be inclined about a pivot shaft 50 which serves as the center of the toroidal-shaped surfaces of the input and output disks 31 and 32. And, lubricant having large viscous frictional resistance is supplied to the contact surfaces between the input and output disks 31, 32 and the power rollers 36a, 37a, whereby power input to the input disk 31 can be transmitted through the films of the lubricant and the power rollers 36a, 37a to the output disk 32.

By the way, the power rollers 36a and 37a are independent of the input shaft 33 (that is, they are not affected directly by the power of the rotary shaft 33) through needles 45. On the output disk 32, there is disposed an output shaft 44 which is arranged in parallel to the input shaft 33 and is rotatably supported on the housing (not shown) through angular-contact bearings 42.

In the present toroidal-type continuously variable transmission 30, the power of the input shaft 33 is transmitted to the loading cam 34. And, in case where this power transmission rotates the loading cam 34, the power caused by the rotation of the loading cam 34 is transmitted through the cam roller 35 to the input disk 31, so that the input disk 31 is rotated. Further, the power generated by the rotation of the input disk 31 is transmitted through the power rollers 36a and 37a to the output disk 32. In response to this, the output disk 32 is rotated integrally with the output shaft 44.

In transmission, the trunnions 40 and 41 may be moved by a slight distance in the direction of the pivot shaft 50. That is, due to the axial-direction movements of the trunnions 40 and 41, intersection between the rotary shafts of the power rollers 36a, 37a and the axes of the input and output disks 31, 32 is slightly shifted. This upsets the balance between the rotational peripheral speed of the power rollers 36a, 37a and the rotational peripheral speed of the input disk 31; and, due to a component force of the rotation drive force of the input disk 31, the power rollers 36a, 37a are inclinkingly rotated around the pivot shaft 50.

Therefore, the power rollers 36a, 37a rotate inclinkingly on the curved surfaces of the input and output disks 31, 32, with the result that a speed ratio is changed, that is, the speed is reduced or increased.

Here, Table 2 shows the results of the above-mentioned evaluation.

TABLE 2

|  | Kinds of Steel | Detected Defect | Breaking Time (hours) |
| --- | --- | --- | --- |
| Example 1 | SCR440 | No Defect | No Breakage |
| Example 2 | SCR420 | No Decect | No Breakage |
| Example 3 | SCR420 | Defect (50 um) is detected. | No Breakage |
| Comparison Example 1 | SCR420 | One Defect is detected | 206 (hrs.) |
| Comparison Example 2 | SCR420 | Four Defects are detected. | 53 (hrs.) |

In Table 2, an embodiment 1 is a disk which is formed of SCR 440, whereas an embodiment 2 is a disk which is formed of SCR 420; that is, they are different in the kinds of steel from each other. However, in both of them, there were not detected any defect a size of 100 μm or more, and, referring to the breaking lives (durability life) of them, no damage or breakage was found in them even after use of more than 500 hours.

Also, an embodiment 3 is a disk in which one defect having a size of 50 μm was detected by the ultrasonic defect detection. However, similarly to the embodiments 1 and 2, no damage or breakage was found even after use of more than 500 hours.

On the other hand, in a comparison example 1, a defect having a size of 100 μm was detected, and the breaking life of the comparison example 1 was found 206 hours. And, the broken position of the comparison example 1 coincided with the defect position thereof.

Further, in a comparison example 2, one defect having a size of approx. 500 μm and three defects each having a size of 100 μm were detected. The breaking life of the comparison example 2 was short, that is, only 53 hours.

By the way, the broken position of the comparison example 2 coincided with the detected position of the defect having a size of approx. 500 μm.

Now, FIG. 5 is a graphical representation of the characteristics of the samples, in which the horizontal axis shows defect sizes (μm) and the vertical axis shows the breaking lives (hours) of the samples; and FIG. 5 shows the relations between the sizes of the defects found in the depth of 0.5 mm from the surfaces of the samples and the breaking lives of the samples. According to the results of the evaluation, the breaking lives of the respective samples are as follows: that is, in the case of a defect having a size of 51 μm, the breaking life of the sample is 300 hours or longer; in the case of a defect having a size of 72 μm, the breaking life of the sample is approx. 300 hours; in the case of a defect having a size of 93 μm, the breaking life of the sample is approx. 288 hours; in the case of a defect having a size of 101 μm, the breaking life of the sample is approx. 203 hours; in the case of a defect having a size of 115 μm, the breaking life of the sample is approx. 122 hours; in the case of a defect having a size of 131 μm, the breaking life of the sample is approx. 83 hours; in the case of a defect having a size of 154 μm, the breaking life of the sample is approx. 72 hours; in the case of a defect having a size of 203 μm, the breaking life of the sample is approx. 61 hours; in the case of a defect having a size of 257 μm, the breaking life of the sample is approx. 49 hours; in the case of a defect having a size of 309 μm, the breaking life of the sample is approx. 41 hours; and, in the case of a defect having a size of 505 μm, the breaking life of the sample is approx. 28 hours. This shows that, in case where the defect size exceeds 100 μm (0.1 mm), the breaking lives of the samples are lowered sharply and heavily.

Now, FIG. 6 is a graphical representation of the characteristics of the samples, in which the horizontal axis expresses distances (defect positions) (mm) from the surfaces of the samples and the vertical axis expresses the breaking lives (hours) of the samples; and FIG. 5 shows the relations between the positions of defects (defect size of 100 μm) and the breaking lives of the samples. According to the results of the evaluation, the breaking lives of the respective samples are as follows: that is, in the case of a defect position of 0.11 mm, the breaking life of the sample is approx. 31 hours; in the case of a defect position of 0.23 mm, the breaking life of the sample is approx. 43 hours; in the case of a defect position of 0.31 mm, the breaking life of the sample is approx. 55 hours; in the case of a defect position of 0.41 mm, the breaking life of the sample is approx. 60 hours; in the case of a defect position of 0.51 mm, the breaking life of the sample is approx. 153 hours; in the case of a defect position of 0.55 mm, the breaking life of the sample is approx. 210 hours; in the case of a defect position of 0.62 mm, the breaking life of the sample is approx. 254 hours; in the case of a defect position of 0.71 mm, the breaking life of the sample is approx. 277 hours; in the case of a defect position of 0.83 mm, the breaking life of the sample is approx. 291 hours; in the case of a defect position of 0.91 mm, the breaking life of the sample is approx. 300 hours; and, in the case of a defect position of 1.31 mm, the breaking life of the sample is approx. 300 hours. This shows that, in case where a large size defect exists within the distance of 0.5 mm from the surfaces of the samples, the breaking lives of the samples are lowered sharply and heavily.

(Method for Operating an Ultrasonic Defect Detect Test)

Next, description will be given below of a method for operating an ultrasonic defect detect test.

In this method, as the sample 2, there was used the CVT input disk 31. This sample 2 is immersed in the water within the water tank 11 together with a focus-type probe (frequency of 10 MHz, vibrator diameter of 6 mm) serving as the ultrasonic defect detecting probe 3, and, in this state, detection of defects existing in the range down to 2 mm which is deeper than the maximum shearing stress position of the present input disk from the slide surface of the sample 2 as well as detection of defects existing in the deeper range were carried out by means of the rotation of the sample 2 and the movement of the probe 3 in the axial direction of the sample 2, thereby detecting defects over the whole section of the sample 2.

By the way, in the case of the oblique defect detection down to 2 mm from just below of the raceway surface of the sample 2, the water distance (that is, the distance between the inner peripheral surface of the bearing ring 2 and the ultrasonic defect detecting probe 3) was set at 20 mm, and, in the case of the vertical defect detection in the deeper area than 2 mm, the water distance was set at 15 mm.

Figure 7:
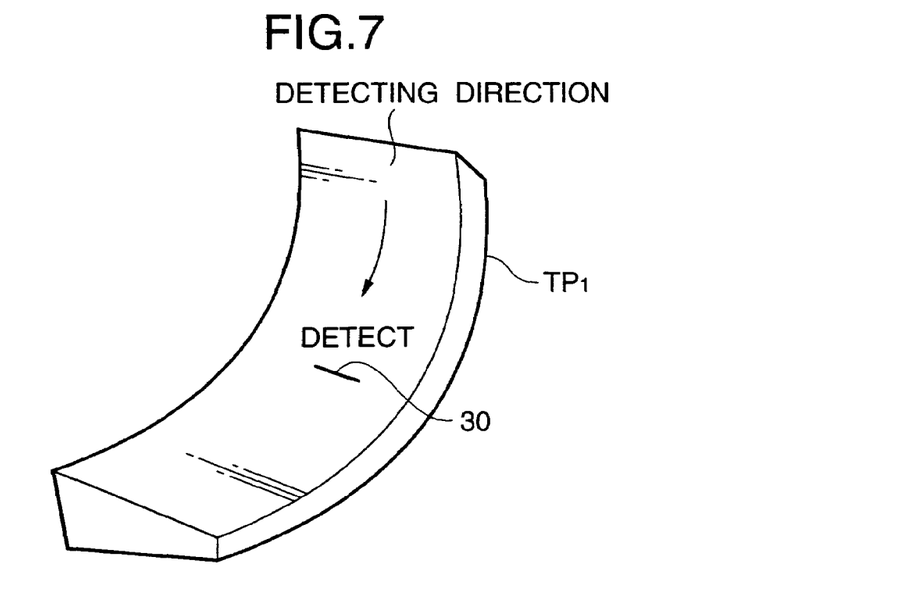
FIG. 7 is a perspective view showing a test piece provided with an artificial defect perpendicularly to a detecting direction (circumferential direction)
Figure 8:
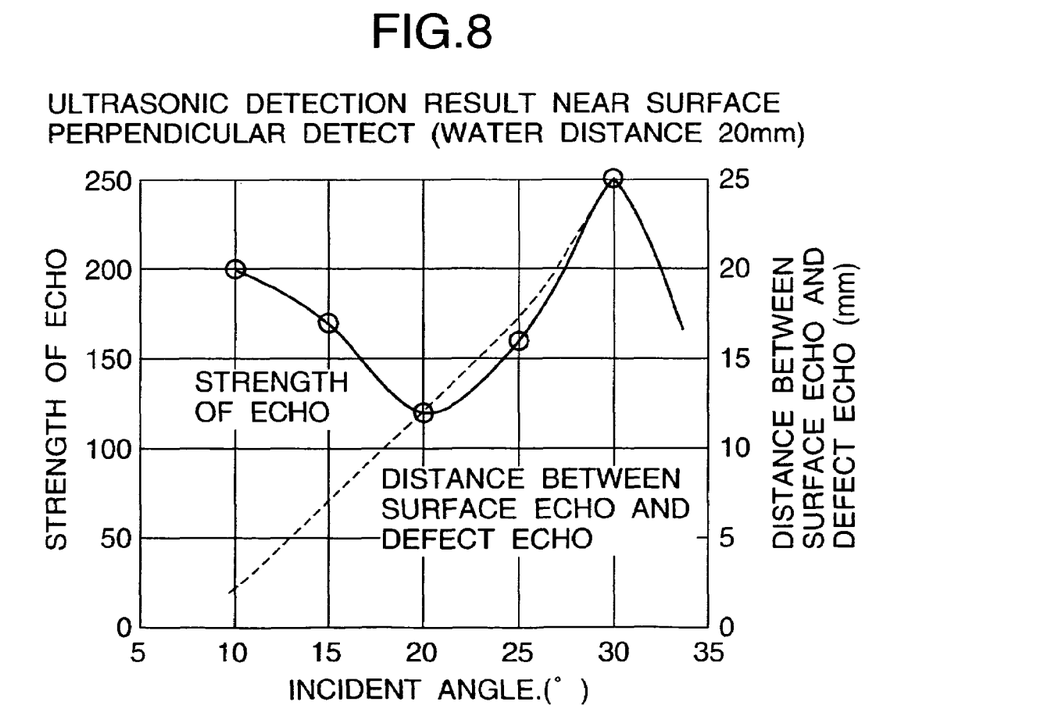
FIG. 8 is a graph showing the detected result in a case of performing the ultrasonic detection as to the test piece shown in FIG. 7.

At first, referring to the detection of a defect in the area down to 2 mm from just below of the raceway surface of the sample 2, as shown in FIG. 7 a test piece including an artificial defect having a length of 10 mm, a width of 0.5 mm and a depth of 0.5 mm was prepared in the raceway surface of the sample 2 in such a manner that it is perpendicular to the defect detect direction (circumferential direction), and, using the ultrasonic defect detect apparatus shown in FIG. 1, the incident angle (that is, an angle at which an ultrasonic wave is inclined in the circumferential direction with respect to a normal on the raceway surface) of an ultrasonic wave transmitted from the ultrasonic defect detecting probe 3 was varied in the range of 5–35° to thereby detect the defect. As a result, as shown in FIG. 8 the artificial defect was detected in the incident angle range of 10–30° by the present oblique defect detection; and, when the incident angle was set at 30°, there could be provided the most sensitive defect detect condition.

Also, in the case of the incident angle of 10° as well, there could be obtained high defect detect sensitivity. However, in this case, a surface echo and a defect echo (a signal to be issued only when a defect exists) are close to each other in position (in the distance of the maximum height). Although they can be visually distinguished from each other, in the case of automatic defect detection, it is difficult to distinguish them from each other. For this reason, it is preferred to employ the condition of the incident angle of 25–30° in which the two echoes are sufficiently distant from each other.

Next, when the defect detection was carried out at the incident angle of 10° (refer FIG. 9) and at the incident angle of 30° (refer FIG. 10), the wave form of a reflected echo displayed on the CRT screen was observed. As a result of this observation, it was found that the distance between the surface echo and defect echo is closer at the incident angle of 10° than at the incident angle of 30°.

Figure 11:
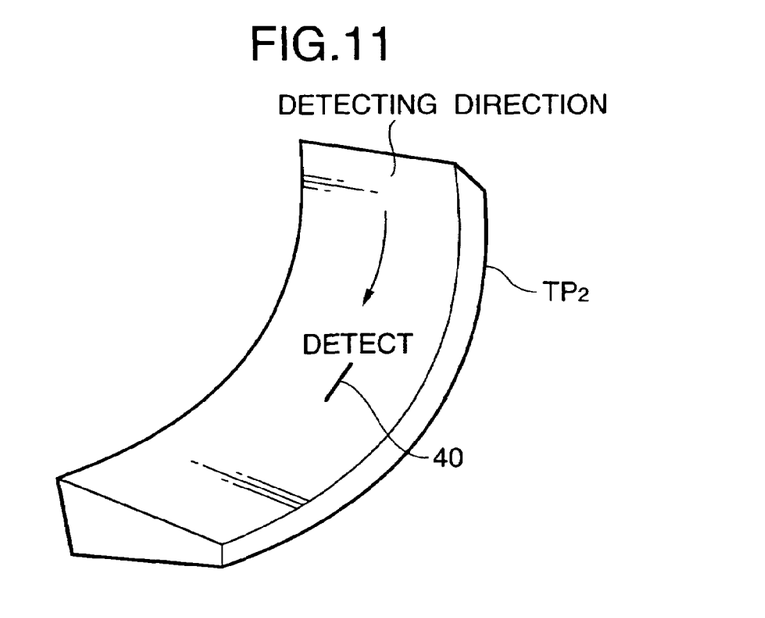
FIG. 11 is a perspective view showing a test piece provided with an artificial defect in parallel to a detecting direction (circumferential direction)

Next, as shown in FIG. 11 a second test piece including an artificial defect having a length of 10 mm, a width of 0.5 mm and a depth of 0.5 mm was prepared in the raceway surface of the sample 2 in such a manner that it is perpendicular to the defect detect direction (circumferential direction), and, using the ultrasonic defect detect apparatus shown in FIG. 1, the incident angle (that is, an angle at which an ultrasonic wave is inclined in the circumferential direction with respect to a normal on the raceway surface) of an ultrasonic wave transmitted from the ultrasonic defect detecting probe 3 was varied in the range of 5–35° to thereby detect the defect.

As a result of this, the artificial defect was detected in the incident angle range of 10–30° by the present oblique defect detection (refer FIG. 12); and, when the incident angle was set at 30°, there could be provided the most sensitive defect detect condition.

Figure 12:
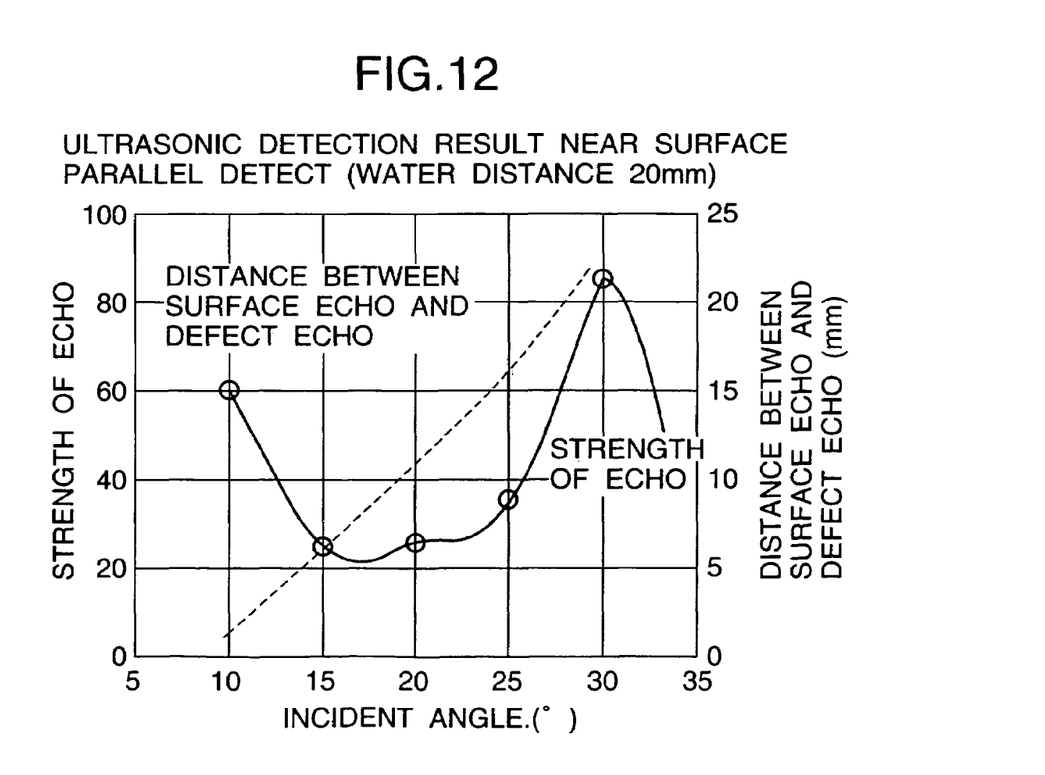
FIG. 12 is a graph showing the detected result in a case of performing the ultrasonic detection as to the test piece shown in FIG. 11.

Also, in the case of the incident angle of 10° as well, there could be obtained a high defect detect sensitivity. However, in this case, the surface echo and defect echo are close to each other in position (in the distance of the maximum height). For a similar reason to the above, it is preferred to employ the condition of the incident angle of 25–30° in which the two echoes are sufficiently distant from each other.

Next, description will be given below of a case where the incident angle is larger than 30° in the oblique defect detect method.

Figure 13:
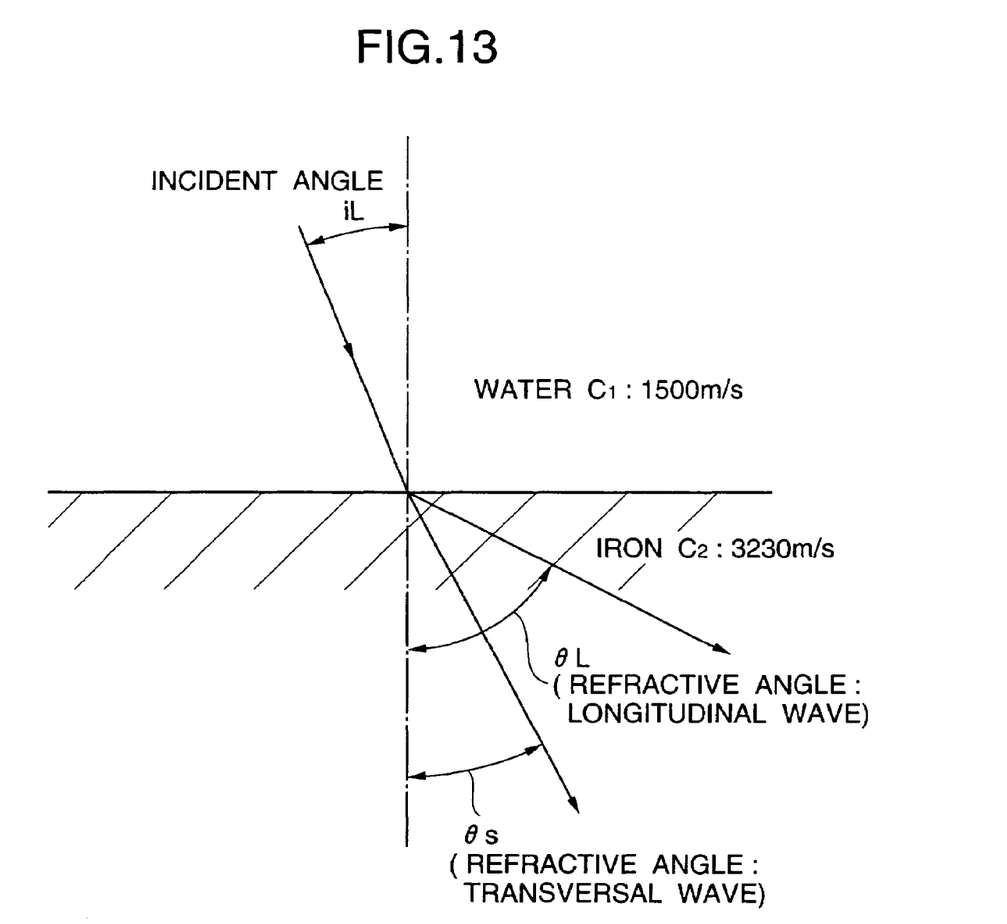
FIG. 13 is a diagram for explaining the relation between an incident angle and a refractive angle when an incident angle exceeds 30 degree.

As clearly shown in FIG. 13, in case where an ultrasonic wave enters a sample formed of iron or steel at an incident angle of $i_L$, it is divided into a transverse wave and a longitudinal wave such that the refraction angle $\theta_L$ of the longitudinal wave>the refraction angle $\theta_s$ of the transverse wave. When an ultrasonic wave is transmitted through water and iron, the incident angle and refraction angle of the ultrasonic wave, when only the transverse wave is observed, have the relations that are shown in the following equations (1) and (2). That is:

$$\sin\theta_s = C_2/C_1 \sin i_L \qquad (1)$$

$$\sin\theta_s = 3230/1500 \sin(i_L) \qquad (2)$$

where $\theta_s < 90°$,
$C_1$: speed of sound in the water 1500 m/s, and
$C_2$: speed of sound in iron 3230 m/s.

The ultrasonic defect detect probe 3 is not only a signal issuer but also a signal receiver. When the ultrasonic defect detect probe 3 receives a signal (a defect signal), the signal returns through a reversed passage (that is, the signal passes through the same passage as the signal issuance reversely). The echo returns to the water from the iron or steel. The signal to be returned may be either a transverse wave or a longitudinal wave, or both of the transverse and longitudinal waves may be returned.

In case where the incident angle of $i_L$ is equal to or more than a certain value, the refraction angle in the steel is equal to or more than 90°, in which a defect signal runs on the surface of the sample or is reflected by the surface so that the defect signal will not return to the ultrasonic defect detect probe 3.

As described above, in the case of the incident angle $i_L$, the refraction angle $\theta_L$ of the longitudinal wave>the refraction angle $\theta_s$ of the transverse wave, and either a transverse wave of $\theta_L$ or a longitudinal wave of $\theta_s$ may be returned. Therefore, we need only to examine the limit of an incident angle at which the longitudinal wave of $\theta_s$ returns.

Figure 9:
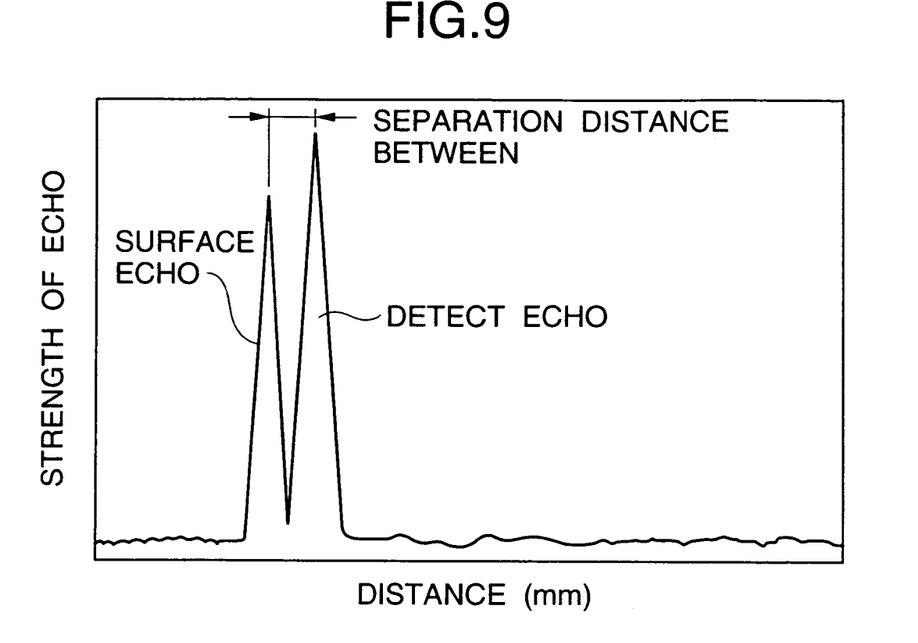
FIG. 9 is a graph showing the relation between a strength of reflection echo and a separation distance between surface echo and defect echo at the time of performing the detection with an incident angle of 10 degree.
Figure 10:
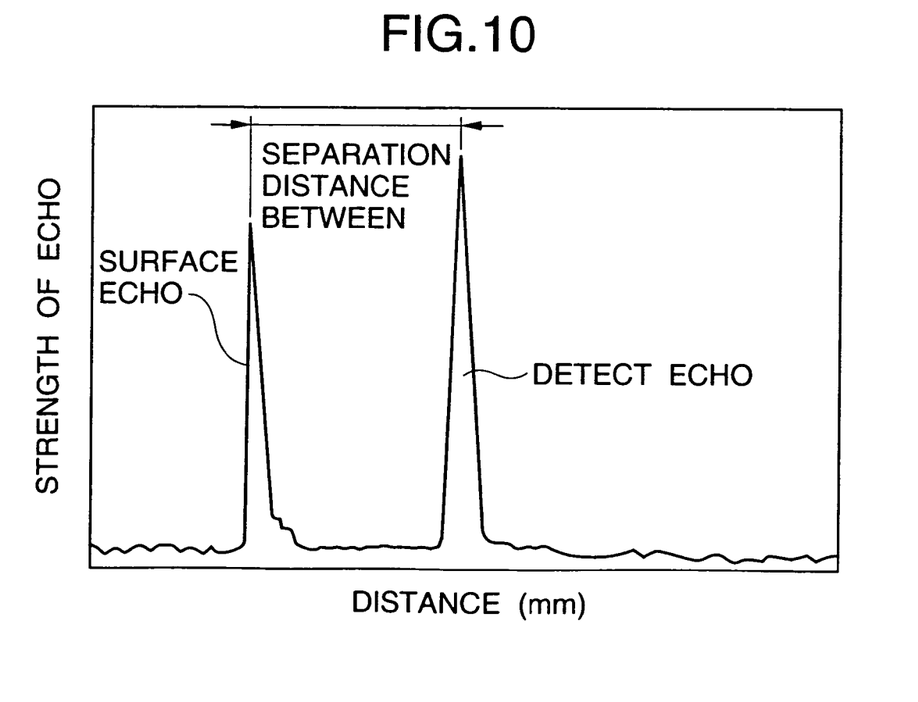
FIG. 10 is a graph showing the relation between a strength of reflection echo and a separation distance between surface echo and defect echo at the time of performing the detection with an incident angle of 30 degree.

The limit of the incident angle at that time, theoretically, assuming that $\theta_s$: 90°, is approx. 28° according to the above equations (1) and (2). However, actually, a sound wave is issued with a certain degree of width and thus defects can be detected sufficiently up to an incident angle of 30° Therefore, as shown in FIGS. 8 and 9, in case where the incident angle exceeds 30°, a signal attenuates suddenly. That is, the upper limit of the incident angle in the inclined angle defect detection is 30°.

Next, description will be given below of a defect at a deeper position than 2 mm just below of the raceway surface of the sample 2.

Figure 14:
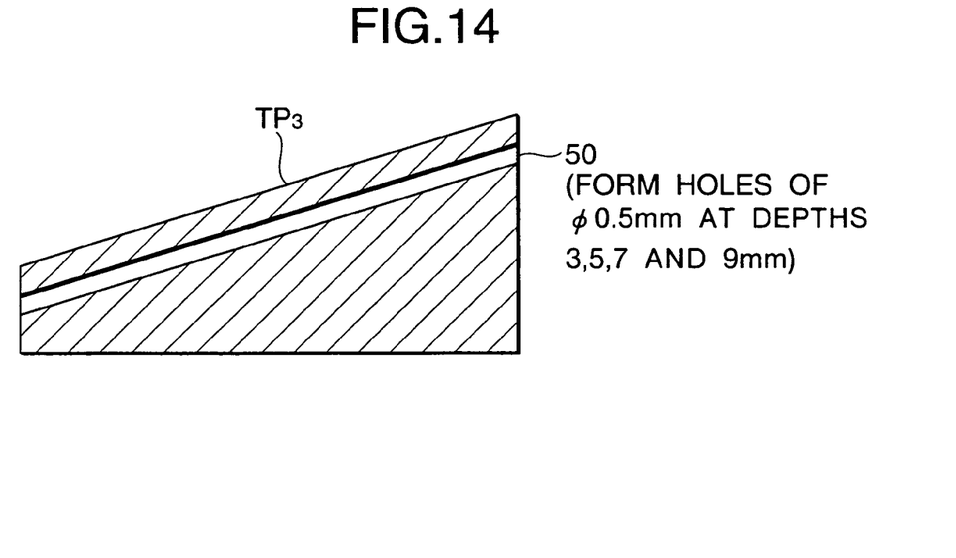
FIG. 14 is a sectional view showing a test piece provided with a hole of 0.5 mm perpendicularly to a detecting direction (circumferential direction) at a predetermined depth from the surface of the piece.

As shown in FIG. 14, a third test piece 50 including three individual holes (artificial defects) of φ 0.5 mm respectively at depth positions of 3, 5 and 9 mm was prepared in the raceway surface of the bearing ring or sample 2 in such a manner that it was perpendicular to the defect detect direction (circumferential direction), and, using the ultrasonic defect detect apparatus shown in FIG. 1, the incident angle (an angle at which an ultrasonic wave is inclined in the circumferential direction with respect to a normal on the raceway surface) of an ultrasonic wave transmitted from the ultrasonic defect detecting probe 3 was varied in the range of 0–30° to thereby detect the defects of the test piece.

As a result of this, all of the artificial defects could be properly detected in the incident angle range of 0–10° in the perpendicular defect detection; and, for all of the defects at the three positions, when the incident angle was set in the range of 0–5°, there could be provided the most sensitive defect detect condition. (Refer FIG. 15.)

Figure 15:
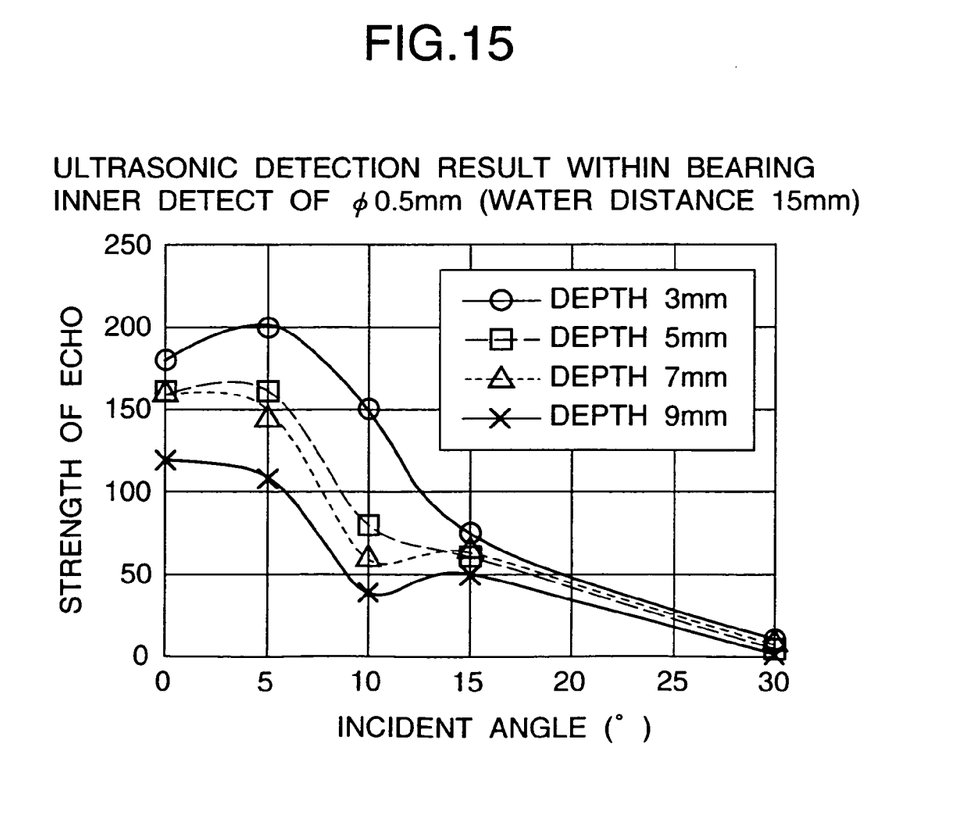
FIG. 15 is a graph showing the detected result in a case of performing the ultrasonic detection as to the test piece shown in FIG. 14.

This shows that the incident angle may be preferably set in the range of 0–5°. Also, when the incident angle is 0° the propagation of the vertical wave provides the shortest distance with respect to the defect, and thus the distance between the surface echo and defect echo is shortened. Therefore, the incident angle may preferably be inclined to a certain degree; and, most preferably, the incident angle may be set at an angle of 5°.

Next, in addition to the detecting method as shown in FIGS. 2 and 3, other concrete examples for detecting and evaluating a defect of the toroidal-type continuously variable transmission components will be briefly explained.

As a rolling member of the toroidal-type continuously variable transmission, there are an input disk, an output disk, an inner ring of a power roller bearing, and an outer ring of the power roller bearing.

Figure 16A:
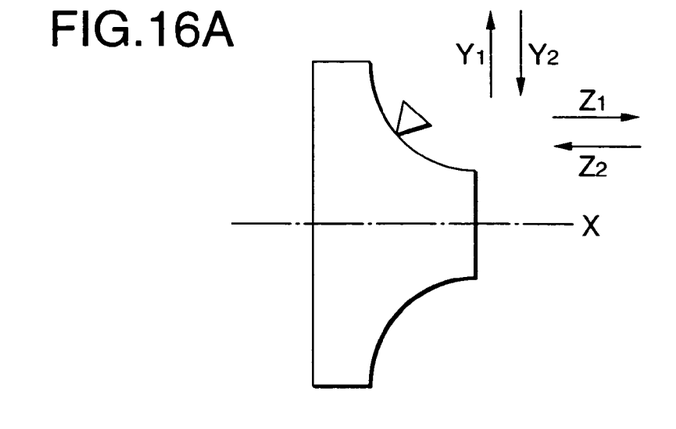
FIGS. 16A, 16B and 16C shows modified examples of method for detecting and evaluating an input or output disk, an inner ring of a power roller and an outer ring of the power roller slider, respectively.

As shown in FIG. 16A, an desired area below the surface to be measured of the input or output disk is detected by the ultrasonic detection probe (not-shown), while the input or output disk is rotated around its rotation axis X and the ultrasonic detection prove (not-shown) is moved away from or close to the disk so as to keep a predetermined interval therebetween a positional controller (not-shown). That is, the area together with the entire surface to be measured is scanned and detected while the probe is moved relative to the disk not only in a direction parallel with the rotation axis X but also in a direction perpendicular to the rotation axis X as shown in arrows Y1, Y2, Z1 and Z2.

Figure 16B:
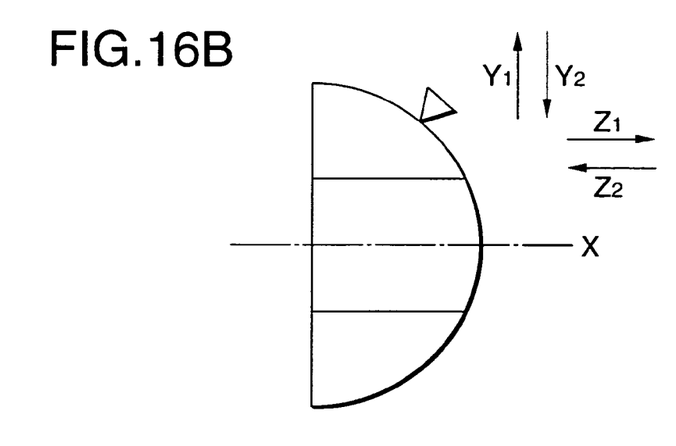

As well as the detection of the disk, with reference to FIG. 16B, the desired area below the surface to be measured of the inner ring of the power roller is detected by the ultrasonic detection probe (not-shown) while the input or output disk is rotated around its rotation axis X and the ultrasonic detection prove (not-shown) is moved away from or close to the disk so as to keep a predetermined interval therebetween a positional controller (not-shown). That is, the area together with the entire surface to be measured is scanned and detected while the probe is moved relative to the disk not only in a direction parallel with the rotation axis X but also in a direction perpendicular to the rotation axis X as shown in arrows Y1, Y2, Z1 and Z2.

Figure 16C:
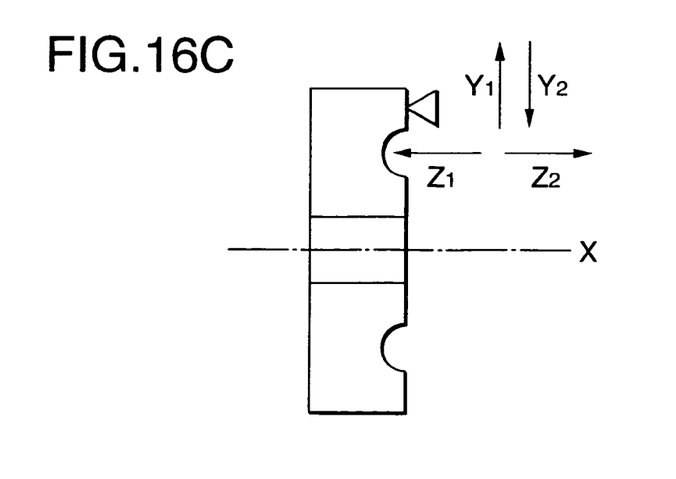

Further, as well as the detection of the disk, with reference to FIG. 16C, the desired area below the surface to be measured of the outer ring of the power roller is detected by the ultrasonic detection probe (not-shown) while the input or output disk is rotated around its rotation axis X and the ultrasonic detection prove (not-shown) is moved away from or close to the disk so as to keep a predetermined interval therebetween a positional controller (not-shown). That is, the area together with the entire surface to be measured is scanned and detected while the probe is moved relative to the disk not only in a direction parallel with the rotation axis X but also in a direction perpendicular to the rotation axis X as shown in arrows Y1, Y2, Z1 and Z2.

According to the invention, there can be supplied a CVT disk which can realize the limited number of large-size inclusions of 100 μm or more in the vicinity of the surface thereof having a relatively large bending stress value by selecting the material of the CVT disk using non-destructive inspection and is thereby outstandingly enhanced in reliability.

While there has been described in connection with the preferred embodiment of the invention, it will be obvious to those skilled in the art that various changes and modifications may be made therein without departing from the invention, and it is aimed, therefore, to cover in the appended claim all such changes and modifications as fall within the true spirit and scope of the invention.

What is claimed is:

1. A process for testing a continuously variable transmission component comprising:
    providing at least one of an input disk and an output disk comprising a contact surface for contacting with another transmission component, said at least one of an input disk and an output disk being made of steel and having a region from the surface formed at 0.4 mm or less from the contact surface thereof;
    measuring, by non-destructive inspection, the size of non-metallic inclusions in said region from the surface of said at least one of an input disk and an output disk; and
    determining the at least one of an input disk and an output disk to be an acceptable continuously variable transmission component when the region from the surface does not contain a non-metallic inclusion having the maximum diameter of 0.115 mm or more.

2. A process for testing a continuously variable transmission component comprising:
    providing at least one of an input disk and an output disk comprising a contact surface for contacting with another transmission component, said at least one of an input disk and an output disk being made of steel and having a region from the surface formed at 0.5 mm or less from the contact surface thereof;
    measuring, by non-destructive inspection, the size of non-metallic inclusions in said region from the surface of said at least one of an input disk and an output disk; and
    determining the at least one of an input disk and an output disk to be an acceptable continuously variable transmission component when the region from the surface does not contain a non-metallic inclusion having the maximum diameter of 0.1 mm or more.

3. A method for evaluating a continuously variable transmission component, said method comprising:
    providing at least one of an input disk and an output disk comprising a contact surface for contacting with another transmission component, said at least one of an input disk and an output disk being made of steel and having a region from the surface formed at 0.5 mm or less from the contact surface thereof;
    disposing a desired surface of said at least one of an input disk and an output disk to be measured and an ultrasonic detection probe within an ultrasonic wave transmissive medium;
    transmitting an ultrasonic wave, having a frequency in the range of 5 MHz–30 MHz, from said ultrasonic detection probe to said at least one of an input disk and an output disk through said ultrasonic wave transmissive medium;
    detecting and evaluating a non-metallic inclusion existing in the area of 0.5 mm or less from said desired surface of said at least one of an input disk and an output disk in accordance with an ultrasonic echo reflected by said at least one of an input disk and an output disk; and
    disqualifying said at least one of an input disk and an output disk when the thus detected non-metallic inclusion has the maximum diameter of 0.1 mm or more.

4. The method according to claim 3, wherein said ultrasonic wave is transmitted to said at least one of an input disk and an output disk according to at least one of an oblique defect detect method and a vertical defect detect method.

5. The method according to claim 3, wherein said oblique defect detect method is performed under the condition that an incident angle with respect to said desired surface of said at least one of an input disk and an output disk is in a range of 10 degree to 30 degree and said vertical defect detect method is performed under the condition that an incident angle with respect to said surface of said bearing ring is in a range of 0 degree to 10 degree.

6. The method according to claim 3, wherein said detecting and evaluating step comprises:
    rotating the at least one of an input disk and an output disk about its rotation axis.

7. The method according to claim 3, wherein said detecting and evaluating step further comprises:
    moving said probe so as to keep a predetermined distance between said at least one of an input disk and an output disk and said probe.

8. The method according to claim 3, wherein said detecting and evaluating step comprises:
    rotating the at least one of an input disk and an output disk about its rotation axis; and
    relatively moving said at least one of an input disk and an output disk and said probe along its rotation axis and in a direction substantially perpendicular to said rotation axis so as to keep a predetermined distance between said desired surface of said at least one of an input disk and an output disk to be measured and said probe,
    whereby all of said desired surface of said at least one of an input disk and an output disk is scanned by said probe.

* * * * *